United States Patent
Logel et al.

(10) Patent No.: US 9,823,234 B2
(45) Date of Patent: Nov. 21, 2017

(54) DISPENSING DEVICE FOR HOLDING AND DISPENSING STRIP-LIKE OBJECTS

(71) Applicant: CLARIANT PRODUCTION (FRANCE) S.A.S., Choisy le Roi (FR)

(72) Inventors: Valere Logel, Levallois Perret (FR); Dominique Bois, Montreuil aux Lions (FR)

(73) Assignee: CLARIANT PRODUCTION (FRANCE) S.A.S., Choisy le Roi (FR)

( * ) Notice: Subject to any disclaimer, the term of this patent is extended or adjusted under 35 U.S.C. 154(b) by 0 days.

(21) Appl. No.: 14/765,418

(22) PCT Filed: Feb. 3, 2014

(86) PCT No.: PCT/EP2014/051997
§ 371 (c)(1),
(2) Date: Aug. 3, 2015

(87) PCT Pub. No.: WO2014/118359
PCT Pub. Date: Aug. 7, 2014

(65) Prior Publication Data
US 2015/0377855 A1 Dec. 31, 2015

(30) Foreign Application Priority Data
Feb. 4, 2013 (EP) .................................... 13305127

(51) Int. Cl.
*G01N 33/487* (2006.01)
*B65D 83/08* (2006.01)

(52) U.S. Cl.
CPC ....... *G01N 33/487* (2013.01); *B65D 83/0829* (2013.01); *G01N 33/48757* (2013.01); *G01N 33/48778* (2013.01); *B65D 2583/082* (2013.01)

(58) Field of Classification Search
None
See application file for complete search history.

(56) References Cited

U.S. PATENT DOCUMENTS

| 697,798 A | 4/1902 | Brooks |
| 2,173,046 A | 9/1939 | Smith |

(Continued)

FOREIGN PATENT DOCUMENTS

| EP | 0756567 B1 | 10/1998 |
| EP | 1352611 A1 | 10/2003 |

(Continued)

OTHER PUBLICATIONS

International Search Report with Written Opinion of the International Searching Authority, dated Apr. 28, 2014, with respect to International Application No. PCT/EP2014/051997.

(Continued)

*Primary Examiner* — Gene Crawford
*Assistant Examiner* — Ayodeji Ojofeitimi
(74) *Attorney, Agent, or Firm* — Scott R. Cox

(57) ABSTRACT

A dispensing device for holding and dispensing strip-like objects, like test strips for analyzing a sample of bodily fluid, wherein the dispensing device holds a stack of strips. The dispensing device includes a container portion for holding the stack of strips and a dispenser portion for dispensing strips from the dispensing device, one at a time. The dispenser portion includes a movable element for applying a rotation motion to a strip to be dispensed from a first orientation, in which the strip is enclosed in the dispensing device, to a second orientation, in which the strip is at least partially exposed.

13 Claims, 6 Drawing Sheets

(56) References Cited

U.S. PATENT DOCUMENTS

| | | | |
|---|---|---|---|
| 2,588,152 A | 3/1952 | Newman |
| 2,918,167 A | 12/1959 | Lowen |
| 3,276,622 A | 10/1966 | Krzyzanowski |
| 3,435,988 A | 4/1969 | Jonas et al. |
| 3,516,536 A | 6/1970 | Ino |
| 3,517,855 A | 6/1970 | Hillis |
| 3,581,934 A | 6/1971 | Sciascia |
| 3,899,104 A | 8/1975 | Kohner |
| 3,921,851 A | 11/1975 | Nilson |
| 4,071,165 A | 1/1978 | Leopoldi |
| 4,228,920 A | 10/1980 | Burton |
| 4,240,564 A | 12/1980 | Pritchard |
| 4,266,690 A | 5/1981 | Holmes et al. |
| 4,420,079 A | 12/1983 | Gliniorz et al. |
| 4,530,447 A | 7/1985 | Greenspan |
| 4,573,632 A | 3/1986 | Scheeren |
| 4,653,668 A | 3/1987 | Gibilisco et al. |
| 4,782,981 A | 11/1988 | Schuster |
| 4,784,556 A | 11/1988 | Ackeret |
| 5,505,308 A | 4/1996 | Eikmeier et al. |
| 5,687,876 A | 11/1997 | Lucas, Jr. |
| 5,736,616 A | 4/1998 | Ching et al. |
| 5,788,064 A | 8/1998 | Sacherer et al. |
| 5,791,515 A | 8/1998 | Khan et al. |
| 6,082,581 A | 7/2000 | Anderson |
| 6,334,974 B1 | 1/2002 | Chen |
| 6,497,845 B1 | 12/2002 | Sacherer |
| 6,508,380 B1 | 1/2003 | von Schuckmann |
| 6,619,494 B1 | 9/2003 | Brozell et al. |
| 6,832,697 B2 | 12/2004 | Lai |
| 7,287,666 B2 | 10/2007 | De Laforcade |
| 7,428,978 B2 | 9/2008 | Lewis et al. |
| 7,628,292 B2 | 12/2009 | Lancesseur et al. |
| 8,906,305 B2 * | 12/2014 | Brenneman ...... G01N 33/48757 221/102 |
| 2002/0057993 A1 | 5/2002 | Maisey et al. |
| 2003/0010668 A1 | 1/2003 | Taskis et al. |
| 2003/0106900 A1 | 6/2003 | Storz |
| 2003/0121932 A1 | 7/2003 | Wajda |
| 2004/0178216 A1 | 9/2004 | Brickwood et al. |
| 2005/0061706 A1 | 3/2005 | Reynolds et al. |
| 2006/0169603 A1 | 8/2006 | Lancesseur et al. |
| 2006/0182656 A1 * | 8/2006 | Funke .............. G01N 33/48757 422/400 |
| 2007/0173739 A1 | 7/2007 | Chan |
| 2008/0182656 A1 * | 7/2008 | Crowder, Jr. ........... A63F 13/08 463/25 |
| 2009/0014463 A1 | 1/2009 | Brozell |
| 2009/0098018 A1 | 4/2009 | Bainczyk et al. |
| 2010/0041156 A1 | 2/2010 | Brenneman et al. |
| 2011/0147244 A1 | 6/2011 | Chan et al. |

FOREIGN PATENT DOCUMENTS

| | | |
|---|---|---|
| EP | 1799581 B9 | 6/2008 |
| FR | 892608 | 5/1944 |
| FR | 2624106 A1 | 6/1989 |
| FR | 2709475 A3 | 3/1995 |
| GB | 539891 | 9/1941 |
| GB | 1074165 | 6/1967 |
| GB | 2092108 A | 8/1982 |
| GB | 2118146 A | 10/1983 |
| GB | 2210603 A | 6/1989 |
| JP | 9315455 A | 12/1997 |
| JP | 2003118758 A | 4/2003 |
| WO | WO9409084 A1 | 4/1994 |
| WO | WO9528338 A1 | 10/1995 |
| WO | WO9851758 A1 | 11/1998 |
| WO | WO9948963 A2 | 9/1999 |
| WO | WO2004024593 A1 | 3/2004 |

OTHER PUBLICATIONS

Search Report dated May 25, 2017 issued by State Intellectual Property Office (SIPO) with respect to parallel Chinese patent application No. 201480007189.5.

* cited by examiner

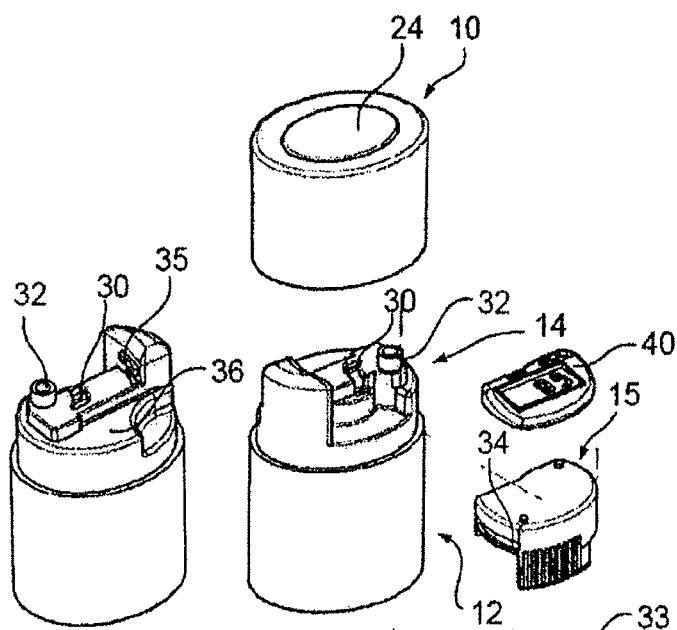
Fig. 5A
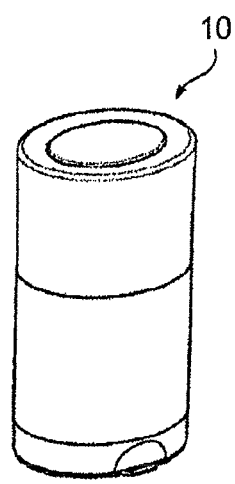
Fig. 6
Fig. 5B
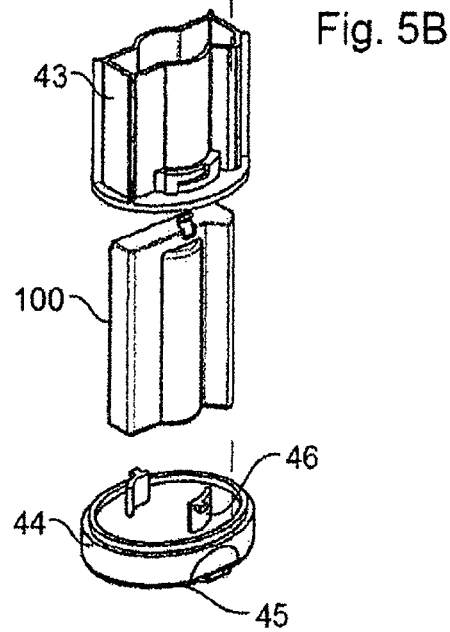
Fig. 5

DISPENSING DEVICE FOR HOLDING AND DISPENSING STRIP-LIKE OBJECTS

TECHNICAL FIELD

The invention relates to a dispensing device for holding and dispensing strip-like objects like nutriments or test strips for analyzing a sample of bodily fluid, the dispensing device being configured to hold a stack of such strips. The dispensing device includes a container portion for holding the stack of strips and a dispenser portion for dispensing strips from the dispensing device, one at a time.

PRIOR ART

Glucose monitoring is part of the everyday life of diabetic individuals and the accuracy of the monitoring is essential for these patients. A diabetic patient generally measures blood glucose levels several times a day to monitor and control blood sugar levels. Serious diabetes-related complications, including cardio vascular disease, kidney disease, nerve damage and blindness can result from a failure to test blood glucose levels accurately and on a regular basis. In order to permit a diabetes patient testing the glucose level in a small sample of blood, there are a number of glucose meters.

Some of these glucose meters use disposable test strips having an electronic system and a reactive portion for electronically evaluating the glucose level of the patient's blood. These test strips are usually of an elongated shape, mostly rectangular, with a longitudinal dimension and a cross dimension. When using the glucose meter, the patient first pricks a finger or other body part using a lancing device to produce a small sample of blood or interstitial fluid to be transferred to the reactive portion on the test strip of the glucose meter. The required (single use) test strips are contained in a vial of test strips. Each test strip must be removed and inserted into the glucose meter.

Commonly known simple vials holding multiple strips are disadvantageous. One disadvantage of such vials is that it is not easy to access the strips in the vial. Further, because it is usually not possible to grip exactly one of the strips without touching also other strips, the remaining strips within the vial are usually contaminated when being contacted by the user's fingers.

In order to overcome these drawbacks, EP 1 352 611 B1 describes a test strip vial which is designed to store a number of test strips in a compact manner and can be operated to dispense even small strips, one at a time, as required by a user. The test strip vial of the prior art is, however, dispensed from the vial in the longitudinal orientation of the test strip by pushing the test strip out of the vial. This is achieved by a slider applied to the vial.

The dispensing mechanism of the prior art for dispensing the test strip in its longitudinal direction by longitudinally pushing it out of the vial is unfavorable because the test strip sometimes is deformed or bends when being pushed along the longitudinal direction, and the dispensing opening of the vial might then be blocked by the test strip. Further, there is the disadvantage in the prior art that satisfying tolerances for such a dispenser mechanism is difficult to achieve, requires complicated systems with numerous pieces and high manufacturing costs, yet not being sufficiently reliable.

Further, guiding surfaces are used to extract the strip in its lengthwise direction and these surfaces need to be long enough to avoid undesired motion of the strip. On the one hand, a distance between opposing strip guiding surfaces needs to be slightly greater than the strip dimensions so as to provide a gap which is required for the strip to glide. On the other hand, this gap allows the strip to slightly move around an axis which is perpendicular to a plane of extraction of the strip. The shorter the guiding surfaces are the greater is the possible range of such uncontrolled movement of the strip which will result in a poor accuracy of strip dispensing and blockage.

Therefore, the prior art devices require very tight tolerances in terms of dimension, shape and position of both the guiding surfaces as well as the strip thickness and flatness to achieve a reliable strip dispensing. This, in turn, makes the device less compact than the simple vial constructions mentioned before.

SUMMARY OF THE INVENTION

In view of the above problems of the prior art, it is an object of the present invention to provide a dispensing device of the above-identified technical field which overcomes these problems. In particular, it is an object of the present invention to provide a dispensing device for holding and dispensing strip-like objects, like strips for analyzing a sample of bodily fluid, wherein the dispensing device is configured to hold a stack of strips and includes a container portion for holding the stack of strips and a dispenser portion for dispensing strips from the dispensing device, one at a time, which prevents deformation of the strips and blocking of an opening for dispensing the strips. Further, a dispensing device is desired which easily allows for satisfying tolerances and allowances for the dispensing mechanism. An object of the present invention further is to provide a reliable strip dispensing system which makes use of only a very limited number of mechanical components.

A particular object of the invention is providing a dispensing device which is capable to distribute very thin strips, one at a time, without dispensing or dislodging other strips, deforming or damaging them. The dispensing device is desired to be easily manufactured with a minimum number of parts and assembly steps resulting in minimum costs. The strips contained in the dispensing device are to be protected from external influences such as contamination by air or humidity.

This object is solved by the dispensing device according to claim 1 below. Further advantageous features of the invention are referred to in the dependent claims.

According to the present invention, the dispensing device is characterized in that the dispenser portion comprises a movable element for applying a rotational motion to a strip to be dispensed, from a first orientation, in which the strip is enclosed in the dispensing device, to a second orientation, in which the strip is at least partially exposed. The strip rotates in the plane of the strip. In other words, the rotational motion is about an axis of rotation which is perpendicular to the plane of this strip.

The rotational motion of the strip is induced by a movable element of the dispenser portion on a longitudinal side of the strip which avoids sliding the test strip along its longitudinal direction, hence avoiding the risk of bending of the strip. Preferably, a stopper or fulcrum, against which a part of the strip can abut to avoid a transversal sliding motion when the movable element laterally pushes the strip on its longitudinal side and which facilitates inducing the rotational motion, can be provided in the dispenser portion. In this way, the rotational motion of the strip is induced by two forces applied on the two opposite longitudinal sides of the strip, preferably at two different positions along the length of the strip.

From a structural point of view, the dispenser portion can be configured by a combination of a movable element and a recess, or clear space, within the dispenser portion in which a part of the strip can be situated. This clear space can receive a part of the strip to allow the strip to properly rotate. More particularly, the clear space is configured to contain a part of the strip to be dispensed opposed to an end of the strip which is exposed in its second orientation. In a preferred embodiment, the clear space goes over the longitudinal edge of the stack of strips and at least in the plane of the first strip to dispense. The clear space is preferably on the same longitudinal side as the action of the movable element. This clear space can be of any type allowing a strip to be distributed by being properly rotated into a second orientation. Examples for the clear space are a cavity or a laterally, with respect to the axis of rotation of the strip, closed compartment in the dispenser portion or even a gap which defines an opening into which a part of the strip can protrude but without further lateral walls enclosing the clear space in addition to the walls defining the gap or opening as such.

Further, with regard to the tolerances of the dispenser portion, the rotational motion allows for more easily manufacturing a dispenser satisfying high demands concerning tolerances or allowances. In addition, if compared to slidingly pushing the strip out of the dispensing device along the direction of its cross dimension (perpendicular to the direction of the longitudinal dimension), the rotating motion allows for safely dispensing the strip without the risk of the strip being lost because it is easily possible to dispense the strip such that it is still held in the dispensing device.

The dispensing device, in particular container portion, being configured for holding a stack of strips can preferably comprise a spare cartridge intended to contain the stack of strips. Alternatively, the stack of strips can directly be contained in the container portion of the dispensing device. If a cartridge is used, this can preferably be a disposable cartridge for introduction in a non-disposable dispensing device which allows for an easy refilling of the dispensing device with a new stack of strips. This facilitates using the dispensing device over a long period of time while the strips to be dispensed by the dispensing device can easily be refilled.

When the dispensing device comprises no more strips, a cartridge filled with a stack of strips can be separately provided, preferably in a package which is suitable for protecting the cartridge from air and humidity so as to avoid a contamination of the cartridge as far as possible such as, for example, a sealed aluminum pouch.

A preferred feature of such cartridge (and also of the dispensing device as such) is the presence of a clear space in the cartridge and/or the dispensing device allowing the strip to properly rotate when the movable element acts on the strip to rotate the strip for dispensing it. In particular, the clear space is configured to contain a part of a rotating strip opposed to an end of the strip which is exposed in the second orientation in which the strip is dispensed. This clear space can be of any type allowing the strip to properly rotate into the second orientation, for example a cavity, a closed compartment or an opened gap, etc. Furthermore, the clear space can be present over the entire height of the cartridge or only near the dispenser portion, that is to say, in a region configured for a strip to be dispensed from the cartridge in which the strip can take the second orientation. When the clear space is in the form of a closed or partly closed compartment, the design of the cartridge has an asymmetric shape which allows for defining a preferred orientation for the loading of the cartridge into the container portion.

A further preferred feature of the dispensing device or of the cartridge is a window or a gap allowing the passing of a pushing rib of the movable element to facilitate a dispensing action of a strip.

In addition or as an alternative, the dispensing device or the cartridge can preferably comprise a slot for facilitating that only one strip is dispensed at a time.

In addition or as an alternative, the cartridge can comprise and/or be made of desiccant material. The skilled person will understand that each of these features can be realized in the present invention as an independent feature or in combination with further features of the present invention.

Preferably, the movable element is configured to apply a force to a strip to be dispensed by contacting the strip near its middle part in its lengthwise direction and pushing the strip laterally with respect to the lengthwise direction. A first effect is that there is less dispersion of the strain on the width than on the length of the strip avoiding deformation (providing more rigidity of the strip). Further, the strip preferably can be thicker and more rigid in its middle portion than in its lengthwise ends and the strain near the middle part of the strip is more precise. This helps in avoiding a pushing rib to pass below or over the strip to be dispensed.

Further preferably, the stack of strips is pushed against a locating surface in a way that the movable element effectively acts on only one single strip. This locating surface is in a plane that is perpendicular to the axis of rotation of the strip. This locating surface can for example be a wall in the dispenser portion or, if applicable, the top wall of the cartridge. The movable element can comprise an actuating portion, which is configured to be directly actuated by a user, and a rib, which is attached to the actuating portion and is configured to directly contact the strip to be dispensed. In a preferred embodiment, the locating surface comprises a window or a gap allowing the passing of a pushing rib of the movable element. In this manner, the abutment of the pushing rib on only a single strip can be very well and easily defined.

The rib can be designed to be a longitudinally extending, curved element having a first and a second longitudinal end portion. The first longitudinal end portion can be configured to contact the strip. The second longitudinal end portion can be configured to be attached to the actuating portion.

In a preferred embodiment, the dispenser portion is configured for exposing only a part of the strip. It is preferred that the rotational motion of the strip is such that only a part of the strip, for example less than half of the strip, is exposed and thus dispensed from the dispensing device. The remaining part of the strip preferably remains inside the dispensing device until the user grabs the strip for finally removing it from the dispensing device, e.g. for introducing it into the glucose meter. This allows for a particularly safe dispensing action because the only partially exposed strip partially remains within the dispensing device and can hardly be lost. A further advantage of this preferred feature is that a reactive part of the strip can be protected from being contacted by the finger of a user. Hence, avoiding that the strip can fall out of the dispenser portion and protecting a possible reactive part of the strip by letting the strip be partially remaining in the dispenser portion securely protects any sensitive parts of the strip from being contaminated.

As alternatives to the dispenser portion being configured by a combination of a movable element and a recess or clear space within the dispenser portion in which a part of the strip can be situated, also further possibilities exist for the dispenser portion to be configured for exposing only a part of the strip.

According to a preferred embodiment, the dispenser portion and/or the cartridge defines a fulcrum for the rotational motion of the strip. This fulcrum can be defined by the dispenser portion or the cartridge by an edge or a similar element against which the strip can abut upon the application of a force by the movable element for applying the rotational motion. In particular, the fulcrum is located on the longitudinal side of the strip opposed to the longitudinal side on which the force is applied by the movable element. More particularly, the fulcrum is located on the longitudinal side of the strip which is opposed to the clear space. The dispenser portion or the cartridge defining a fulcrum for the rotational motion of the strip allows for a particularly well-defined rotational motion of the strip when operating the movable element of the dispenser portion. Indeed, in this manner, the rotational motion is about an axis of rotation that is situated on a longitudinal side of the strip. More particularly, the axis of rotation is perpendicular to the plane of the strip and is situated on the contact point between the fulcrum and the longitudinal side of the strip.

Preferably, the dispenser portion comprises a recess for facilitating grabbing of the strip in the second orientation by a user. The strip being rotated by the movable element of the dispenser portion is to be grabbed by a user or otherwise taken out of the dispensing device, e.g. for being introduced into a glucose meter or similar device. For facilitating the removal of the strip in the second (final) orientation, the recess is preferably provided at a position of the dispensing device where a portion of the exposed part of the strip is placed, after the rotational motion was applied to the strip by the movable element.

Advantageously, the container portion comprises a spring for applying a spring force to the stack of strips in a spring force direction toward the dispenser portion. A spring for pressing the strips of the stack of strips toward the dispenser portion allows for using the dispensing device in almost any orientation and almost independently from the amount of strips within the container portion. If the spring applies the spring force toward the dispenser portion, the dispenser portion can always cooperate with one strip, if at least one strip is contained within the container portion. The spring can be fixed to the bottom of the container portion or to a similar device such as a cartridge for strips which can be used in the container by any suitable fastening means. As an example, the spring can be simply disposed around a central rod protruding from the internal surface of the bottom of the container portion or similar device. Alternatively, besides other compensation means which are suitable for pressing the strips against the dispenser portion, the spring is not essential for the invention but dispensing the strips from the dispensing device is also possible if the dispensing device is oriented such that an external force such as gravity acts on the strips to be situated at the dispenser portion such that one of the strips can reliably be dispensed from the dispensing device.

In another preferred embodiment, the cartridge comprises the spring. In such embodiment, the bottom of the cartridge can be attached to the cartridge body, for example by ultrasonic welding, laser welding, snapping and the like.

Preferably, the dispenser portion is configured for applying a rotational motion to the strip about an axis of rotation which is oriented in parallel to the spring force direction. In other words, the strip moves in a plane which is perpendicular to the spring force direction. As an example, the dispenser portion can comprise a protrusion or an opening fitting to a corresponding opening or protrusion in the movable element, defining a rotation axis of the movable element. Hence, the spring force does not act in the extracting direction of the strip but exerts a pressure on the strips perpendicularly to it, which results in a more precise movement of the strip, induced by the movable element, because the spring force minimizes any clearance or play of the dispenser portion. This allows for a dispensing device of a particularly high quality rating.

Further preferably, the container portion comprises a piston which is configured to be pressed by the spring towards the stack of strips. In other words, the piston is situated between the spring and the stack of strips, if strips are contained in the container portion. The piston primarily allows for a particularly even distribution of the spring force to the strips so that the strips can easily be dispensed from the dispensing device without unforeseeable forces acting on the strip to be dispensed. In another preferred embodiment, the piston can be contained in a cartridge. In a further embodiment, the cartridge can comprise the stack of strips and the piston, whereas the spring is located in the container portion.

Further, it is preferable that the piston comprises and/or contains a desiccant material. In one alternative, the piston (itself) can comprise or at least partially be made of a desiccant material. In a second alternative, the piston can contain (separate) desiccant material. Of course, also a combination of the piston comprising, i.e. being made of, and additionally containing a desiccant material is possible. Further, a desiccant material or any other ingredient for active modification of the atmosphere inside of the device can be located anywhere in the device or integrated into any component of the device.

In a preferred embodiment, the container is configured for holding a stack of 25 to 50 strips. This implies an advantageous size of the dispensing device which allows for easy handling.

According to a preferred embodiment, the container portion is of a cylindrical shape, wherein the dispenser portion is situated at one of the two axial ends of the container portion. A cylindrical shape in this context is the shape of any cylinder with a circular or a non-circular base. In particular, also a polygonal regular or irregular base or a composition of curved surfaces and flat surfaces can be used as a base for the cylinder forming the container portion. Preferably, the dispenser portion is similarly shaped in top view such that it can be directly attached to the container portion and be securely connected to it. It is preferred that the base of the container portion, in particular of a part of the container portion which is configured to be attached to the dispenser portion, has a circular or oval shape. This shape facilitates a tightly sealed connection of the dispenser portion and the container portion. However, different shapes are possible, as well. Further, it is possible that the container portion and/or the dispenser portion have parts of different shapes which optionally can merge continuously.

In addition, it is preferred that the dispensing device is provided with a cap covering the dispenser portion for protecting and sealing an opening through which the strip can be dispensed by the rotational motion. The cap preferably is in tight seal contact with a part of the dispenser portion in order to protect it from the external environment. As an example, the cap can comprise a groove/bead corresponding to a bead/groove on the dispenser portion for a better tight seal. Further, the cap can be separated from the container portion or can be connected to the container portion or to the dispenser portion by a hinge or any other connecting means. The cap can also be integrally molded with the container portion or with the dispenser portion (connected by a hinge).

The dispenser portion and the container portion of the dispensing device are preferably molded in one piece.

The container portion is intended to contain the stack of strips. Therefore, it can comprise a guide rail, guide sheath, guide case or guide sleeve having a shape adapted to hold the stack of strips or, if applicable, the cartridge. This guide can be a separate piece from the dispensing device, in particular the container portion, or can be integrally molded with the dispensing device, in particular the container portion. If this guide is a piece distinct of the container portion, it can be fixed to the container portion by any suitable fastening means such as for example ultrasonic welding, laser welding a snap system or the like. Alternatively, it can be integrally molded with the bottom of the dispensing device and the assembly thus provided can be fixed to the container portion by any suitable fastening means, for example after loading a stack of strips or a cartridge.

The bottom of the container portion can be tight sealed to the container portion by any suitable sealing means such as, for example, ultrasonic welding, laser welding or a snap system. In a preferred embodiment, the bottom can be attached to the guide referred to above for example by use of a bayonet system, preferably with a seal, for example a rubber seal.

The movable element can be formed by a push button which can be attached to the dispenser portion by any suitable fastening means, for example by snap-in, heat boutrolage, while it is still freely movable, in particular rotatable. The movable element or push button preferably comprises a rib contacting and pushing a strip on its longitudinal side in a transversal direction, preferably near a middle part in the lengthwise direction of the strip. In a more preferred embodiment, while pushing the first strip, the bottom end of the pushing rib does not interact with the next strip. In this manner, the next strip is not scratched or damaged by the rib. Further, the movable element or push button can comprise a hole or tip fitting to a corresponding tip or hole of the dispenser portion defining a rotation axis of the movable element or push button. This hole or tip can also be used as a fastening means allowing attachment of the movable element or push button to the dispenser portion. In a preferred embodiment, this axis of rotation of the movable element is on the same side as the pushing action of the rib regarding the lengthwise direction of the strip.

The movable element or push button can preferably comprise on its peripheral side a groove or a rib fitting to a corresponding rib or groove provided on the dispenser portion for guiding the movable element or push button during the rotational motion, assisting to maintain it in the horizontal plane of the rotational motion and avoiding a vertical shift.

Further, the movable element or push button can comprise a "return means" allowing the automatic return of the push button in its initial position which is the first orientation of the movable element for allowing resetting a new strip. For example, the return means can be a spring, metallic or plastic, which can be integrally molded with the dispenser' portion or with the push button, an elastic band or other means. Furthermore, this automatic return of the rib before the user grabs the first strip in its second orientation, preserves the next strip from being scratched or damaged by the rib as it does not interact with its bottom end.

The dispenser portion preferably comprises a window or gap allowing the passing and/or guiding of a pushing rib of the movable element. Further, the dispenser portion preferably comprises a slot allowing the dispensing of only one strip at a time.

The slot preferably has a slightly greater thickness more than that of one strip. Further preferably, the thickness of the slot is superior to the thickness of one strip of the stack to be dispensed but inferior to the thickness of two strips thereof.

The slot preferably has a length which is inferior to the length of one strip. Hence, when the strip is pushed, a part of the strip abuts an edge of the dispenser portion and a rotational motion is induced thereby. Preferably, the length of the slot is ½ to 9/10 of the length of one of the strips to be dispensed from the dispensing device.

The bottom of the container portion can preferably comprise a double bottom/placement for used strips and/or for placement of a blood lancet with a hood, preferably a hinged hood. The double bottom can be integrally molded with the bottom or be a separate element.

In a preferred embodiment, the cap can be configured such that the movable element is moved into a predefined position upon closing the cap over the dispenser portion. Such cap is particularly comfortable for a user as the predefined position of the movable element can be such that a strip is dispensed automatically upon closing of the cap. In this case, the user does not need to actuate the movable element separately but the strip can be dispensed such that it can be grasped by the user when the cap is opened the next time.

In particular, the cap can be configured as a pushing element which actuates the dispenser portion, in particular the movable element to dispense a strip. Therefore, the cap can comprise a rib for displacing the movable element or push button, hence inducing a rotation of a strip while the cap is closed such that the strip is available to be gripped by the user at the next opening. The movable element or push button can hence be activated when the cap is put onto the dispenser portion and the dispenser portion is rotated until the cap is completely closed. Then, when the cap is opened the next time, the strip is already partially exposed without requiring further activation of the movable element.

Further advantages, features and objects of the present invention become apparent from the following description and the claims attached hereto.

BRIEF DESCRIPTION OF THE DRAWINGS

FIG. 5 shows a second preferred embodiment of a dispensing device for holding and dispensing test strips in exploded view.

FIG. 5A shows a container portion and a part of a dispenser portion of the second preferred embodiment of FIG. 5.

FIG. 5B shows a movable element for the dispenser portion of the second preferred embodiment of FIG. 5 in exploded view.

FIG. 6 shows a preferred dispensing device in perspective view in a closed state.

FIG. 7A-1 shows a cartridge for the second preferred embodiment of FIG. 5.

FIG. 7A-2 shows the cartridge of FIG. 7A-1 in exploded view.

FIG. 7B-1 and FIG. 7B-2 show another cartridge wherein the clear space is defined by an opening.

FIG. 7B-3 shows a top view of the cartridge of FIG. 7B-1 and 7B-2 wherein the clear space is defined by an opening.

DETAILED DESCRIPTION OF THE DRAWINGS

Figure 1:
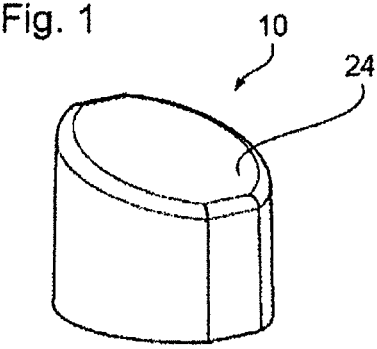
FIG. 1 shows a dispensing device for holding and dispensing test strips according to a preferred embodiment in exploded view.

FIG. 1 shows an exploded view of the dispensing device 10 for holding and dispensing test strips for analyzing a sample of bodily fluid, in particular blood or interstitial fluid. FIG. 1 shows a stack of test strips 16 which is not part of the dispensing device 10, but the dispensing device 10 is configured for holding such a stack of test strips 16 by providing a suitable space for containing it as a stack of preferably 25 to 50 test strips.

Figure 3:
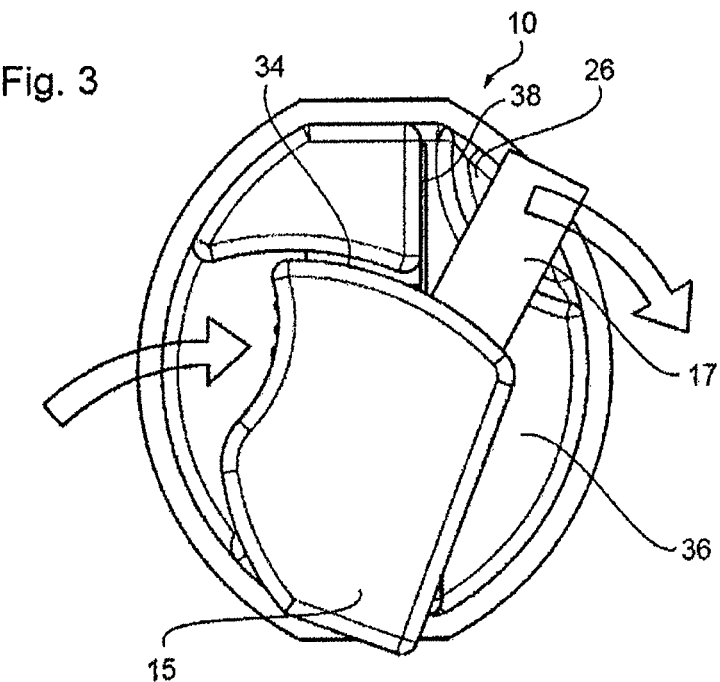
FIG. 3 shows a top view of the dispensing device of FIGS. 1 and 2 indicating the motion for dispensing a test strip.
Figure 4:
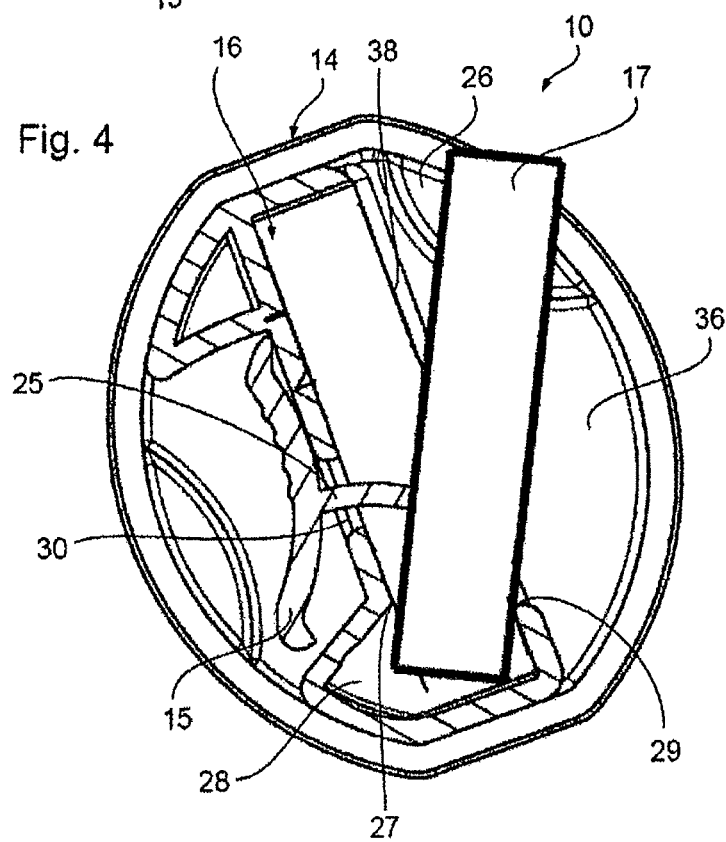
FIG. 4 shows a sectional view of a preferred dispenser portion of a dispensing device illustrated in FIGS. 1 to 3.

The dispensing device 10 comprises a container portion 12 for holding the stack of test strips 16 and a dispenser portion 14 for dispensing test strips from the container 12, one at a time. The container portion 12 has a cylindrical shape, wherein the base shape of the container portion 12 is an oval with two flattened faces, as is also indicated in FIGS. 3 and 4. At one end of the cylindrically shaped container portion 12, the dispenser portion 14 is situated which includes a push button 15 as a movable element for applying a rotational motion to a test strip to be dispensed. The dispenser portion 14 is designed to have a window or gap 30 allowing the passing of a pushing rib (not illustrated in FIG. 1) of the push button for contacting a strip and rotating the strip into the second orientation. Further, the dispenser portion 14 comprises an opening 32 which is configured to house a corresponding tip (not illustrated in FIG. 1) in the push button 15 to form a rotation axis for the push button 15 with respect to the remaining parts of the dispenser portion 14.

Inside the container portion 12, the stack of test strips 16 is supported by a piston 20 which in turn is supported by a spring 18, wherein the spring 18 is adapted to apply a spring force via the piston 20 to the stack of test strips 16 toward the dispenser portion 14. This spring force acts between a bottom 22 of the container portion 12 on the one hand, which bottom 22 is securely fastened to the container body 12, and the piston 20 on the other hand. It is ensured by the spring force generated by the spring 18 that, as long as at least one test strip is contained within the container portion 12, one test strip contacts the dispenser portion 14 and enables the dispenser portion 14 to act on and thereby dispense the test strip. If no such spring 18 is provided in the dispensing device 10, the test strips can alternatively contact the dispenser portion 14 only by means of gravity or another external force.

Finally, the dispensing device 10 is provided with a cap 24 which can be attached to the container portion 12 for it to cover and protect the dispenser portion 14 and the stack of strips 16 contained in the container portion 12 which are generally in communication with the environment via an opening in the dispenser portion 14 which might be present for easily dispensing the test strips.

Figure 2:
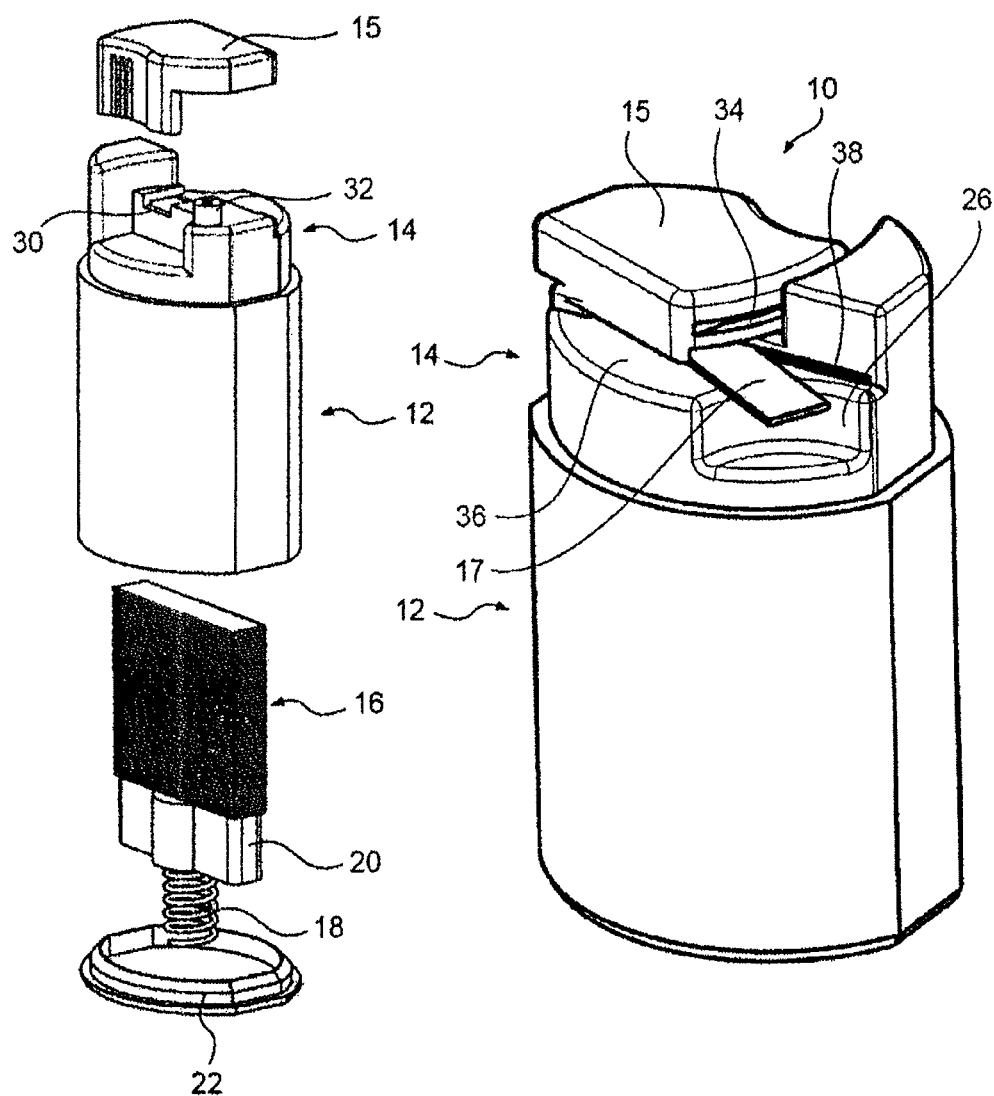
FIG. 2 shows a perspective drawing of the dispensing device of FIG. 1.

FIG. 2 shows a perspective illustration of the dispensing device 10 of FIG. 1 and, as is also the case for FIGS. 3 and 4 and the remaining FIGS. 5 to 10C, the same elements of FIG. 1 are assigned the same reference signs, the description of which thereby being omitted in connection with the further FIGS. 2 to 10C.

In addition to the illustration of FIG. 1, FIG. 2 shows a test strip 17 to be dispensed from the dispensing device 10 which is partially exposed. In other words, only a part of the test strip 17 can be grabbed by a user whereas the remaining part of the test strip 17 is kept within the dispensing device. This remaining part is covered by the push button 15 of the dispenser portion 14 and can be thereby protected. Further, to facilitate grabbing of the exposed test strip 17, which is supported on a guiding surface 36, the dispenser portion 14 comprises a recess 26 which is situated and dimensioned such that the fingers of a user can grab a test strip 17 both from above and below and preferably also from its sides.

Further, FIG. 2 illustrates a groove 34 on the push button 15 which is configured to be engaged by a corresponding protrusion in the dispenser portion 14 (not illustrated) in order to form a guiding means for the push button to facilitate accurately rotating the push button 15 in a defined plane of rotation. FIG. 2 also shows a slot 38 which is dimensioned for allowing only a single strip 17 to be dispensed from the dispensing device 10. In other words, a thickness of the slot 38 is dimensioned slightly larger than the thickness of a strip 17 to be dispensed but smaller than the thickness of two strips so that the slot 38 reliably avoids dispensing of two strips at a time.

FIG. 3 shows a top view of the dispensing device 10 and two arrows in FIG. 3 indicate the movability of the push button 15 and the corresponding rotational motion of the test strip 17 to be dispensed from a first orientation, in which the test strip 17 was (to be plotted in FIG. 3 in the vertical direction), to a second orientation which is actually shown in FIG. 3 and in which the test strip is partially exposed.

FIG. 4 shows a sectional top view similar to the top view of FIG. 3 in which the stack of test strips 16 and its orientation are illustrated. It can be taken from FIG. 4 that the stack of test strips 16 is vertically plotted and that only the test strip 17 to be dispensed was rotated from the orientation of the stack of test strips 16 to the second orientation in which the test strip 17 is partially exposed.

The rotational motion is applied to the test strip 17 by the push button 15, the movable element of the dispenser portion 14. This push button 15 comprise a rib 25 which contacts only the single one test strip 17 to be dispensed, while the other strips of the stack of test strips 16 remain held within the container portion 12. FIG. 4 also illustrates that the rib 25 passes through the window 30 in the dispenser portion 14 of the dispensing device 10.

Further, the dispenser portion 14 illustrated in FIG. 4 further shows an edge 27 and an edge 29 which extend perpendicularly to the plane of the drawing and against which the stack of test strips 16 and the test strip 17 to be dispensed can abut. Moving the push button 15 towards the test strip 17 applies a lateral force to the test strip 17 to be dispensed, wherein the test strip 17 abuts against the edge 29 and rotates thereabout. If, e.g. because of a certain distribution of friction forces acting on the test strip 17 upon application of the lateral force on the test strip 17, the lower part of the strip 17 in FIG. 4 moves so far to the left-hand side in FIG. 4 (backwards rotation), the strip 17 abuts the edge 27 which stops the backwards rotation of the strip 17. In other words, the edge 29 defines a fulcrum for the rotational motion of the test strip 17 to be dispensed, whilst the stopping edge 27 defines, in combination with the edge 29, a maximum rotation angle for the strip 17. Further, the dispenser portion 14 illustrated in FIG. 4 comprises a clear space 28 into which a part of the test strip 17 to be dispensed can reach for it to properly rotate about the fulcrum defined by the edge 29.

FIG. 5 illustrates a second preferred embodiment of a dispensing device 10 for holding and dispensing test strips in exploded view. Most of the elements of this second preferred embodiment are the same as those of the first described preferred embodiment illustrated in FIGS. 1 to 4. In contrast to the first preferred embodiment, the second preferred embodiment illustrated in FIG. 5 comprises a cartridge 100 which holds the stack of strips 16 and forms an exchangeable unit to be introduced into the container portion 12 of the dispensing device 10. The cartridge 100 is further illustrated in FIG. 7 to be described below.

Similar to the first preferred embodiment, the cartridge 100 is contained in the container portion 12 of the dispensing device 10. A sleeve 43 works as a guiding element for the cartridge 100 and ensures a proper insertion of the cartridge 100 into the container portion 12. The sleeve 43 can be attached to a bottom 44 of the container portion 12 by an attachment mechanism, for example a bayonet system 46 illustrated in FIG. 5. In another embodiment (not shown), the sleeve 43 can be integrally molded with the container portion 12. The bottom 44 of the container portion 12 is preferably designed to comprise a double bottom 45 which means that the bottom 44 has an additional space which can be closed by a lid and which can, for example be used to hold used test strips.

Similar to the first preferred embodiment, also the second preferred embodiment comprises an opening 32 which, in cooperation with a corresponding tip (not illustrated in FIG. 5) forms a rotating access for the push button 15 of the dispenser portion 14. FIG. 5 also illustrates the window 30 for the rib 25 of the push button 15.

FIG. 5A shows a container portion 12 and a part of the dispenser portion 14 of the dispensing device 10 according to the second preferred embodiment of FIG. 5. The container portion 12 and partly the dispenser portion 14 are illustrated in perspective view as in FIG. 5 but in a different orientation. FIG. 5A illustrates the opening 32, the window or gap 30, the guiding surface 36 and a ledge 35 which is configured to engage to the groove 34 in the push button 15, illustrated in FIGS. 2, 3 and 5B.

FIG. 5B shows in exploded view the push button 15 as a remaining part of the dispenser portion 12 partly illustrated in FIG. 5A. The push button 15 comprises the groove 34 mentioned before, the rib 25 and a tip 33 which is configured to be housed in the opening 32 on the dispenser portion 14 to form the rotation access for the push button 15 with respect to the main parts of the dispenser portion 14. On top of the push button 15, a control device 40 can be applied. Such control device 40 can, for example, be a monitor or a similar device to determine and indicate results of a measurement on the basis of one of the test strips dispensed from the dispensing device.

FIG. 6 illustrates a preferred dispensing device 10 in perspective view in a closed state. According to this figure, the closed state is taken, when the cap 24 is closed on the container portion 12.

Figures 1, 7A:
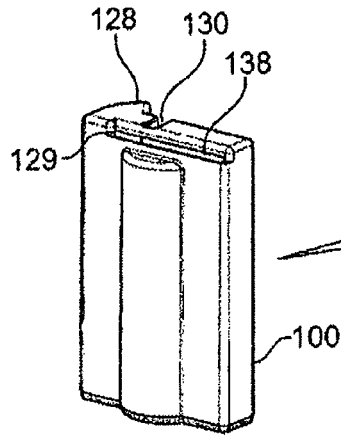
Figures 2, 7A:
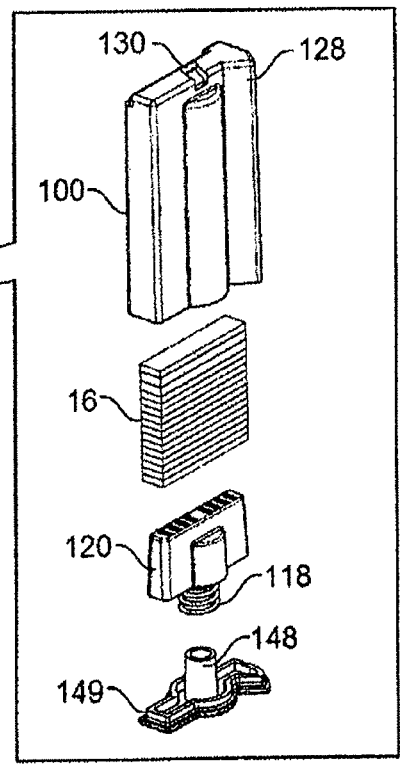
Figures 1, 7B:
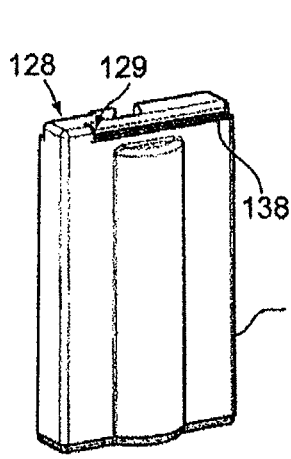
Figures 2, 7B:
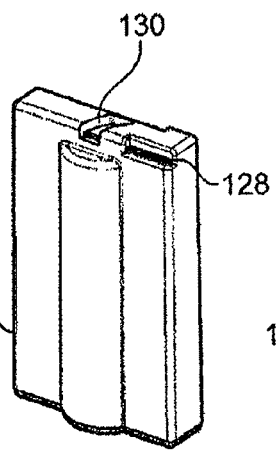
Figures 3, 7B:
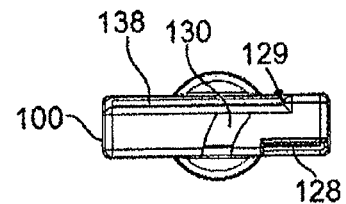

FIG. 7A-1 and FIG. 7A-2 show a cartridge 100 for the second preferred embodiment of FIG. 5. As can be taken from these figures, the cartridge 100 is designed to house a clear space 128 corresponding to the clear space illustrated in FIG. 4 above. Further, the cartridge 100 is configured to house the stack of strips 16. It comprises a fulcrum 129 for the rotational motion of the strip 17 which is on the top of the stack of strips. It also comprises a slot 138 configured to allow only one strip to be dispensed at a time upon actuation of the movable element. Further, cartridge comprises the piston 120 and the spring 118 and is closed by a separate bottom 149. The separate bottom 149 can comprise a pillar 148, which is designed to work as a guiding means for the spring 118 inside the cartridge 100.

FIG. 7B-1, FIG. 7B-2 and FIG. 7B-3 show another embodiment of the cartridge 100 where the clear space 128 is defined by an opening to allow the strip 17 to properly rotate.

Figure 8:
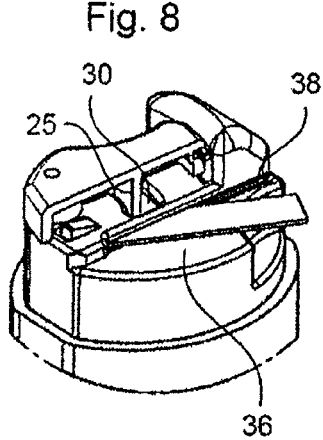
FIG. 8 shows a dispenser portion of a preferred dispensing device in partially sectional view with the movable element and a strip in a second orientation.

FIG. 8 shows a dispenser portion 14 of a preferred dispensing device 10 in partial sectional view in which the push button 15 is in its second orientation so as to dispense a strip 17 from the dispensing device 10. The partly sectional view of FIG. 8 shows that the rib 25 of the push button 15 engages with the strip 17 to be dispensed for it to be rotated. The strip 17 is supported on the guiding surface 36 and the mechanism of the dispensing device 10 is configured to dispense the strip 17 through the slot 38, when the rib 25 abuts and rotates the strip 17. As can also be seen in FIG. 8, the dispensing portion 14 comprises a window or gap 30 to allow the passing of the rib 25 therein.

Figure 9:
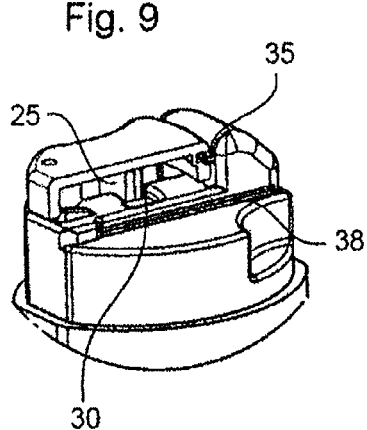
FIG. 9 shows the dispenser portion of FIG. 8 in partial sectional view with the movable element in a first orientation.

FIG. 9 shows the dispenser portion 14 of FIG. 8 in a partial sectional view with the push button 15 in a first orientation. The first orientation of the push button 15 is the orientation in which a strip is not yet exposed. Rather, the rib 25 is positioned to abut a strip of the stack of strips 16 for dispensing it.

Figure 10A:
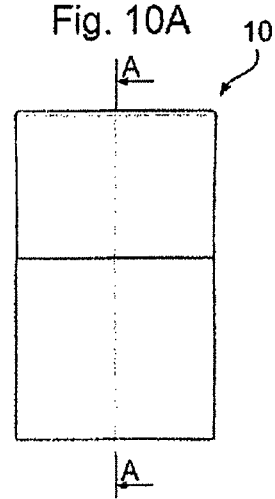
FIG. 10A shows a side view of the dispensing device of the second preferred embodiment.
Figure 10B:
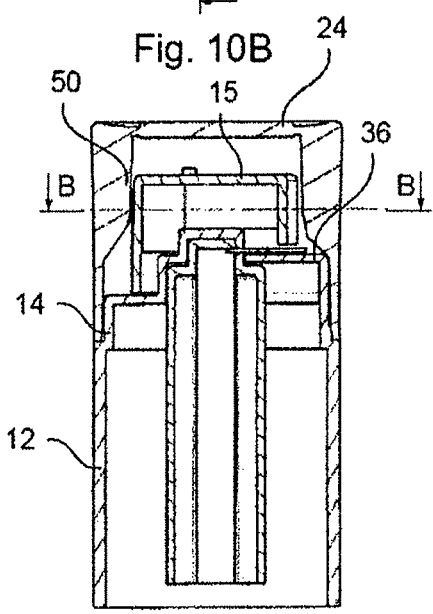
FIG. 10B shows a sectional view of the dispensing device of the second preferred embodiment taken along the plane A-A in FIG. 10A.

FIG. 10A shows a side view of the dispensing device 10 of the second preferred embodiment and illustrates a plane A-A along which the sectional view of FIG. 10B is taken. According to FIG. 10B, the cap 24 is designed to have a rib 50 which, upon closing of the cap 24 onto the container portion 12, actuates the push button 15 of the dispenser portion 14 so that a strip 17 of the stack of strips 16 is rotated into the second orientation for it to be dispensed, when the user opens the cap 24 the next time. The sectional side view of FIG. 10B shows that the rib 50 is designed to increasingly push the push button 15 towards the second orientation.

Figure 10C:
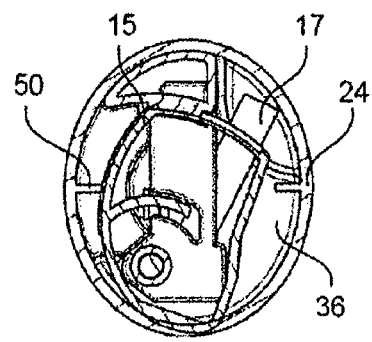
FIG. 10C shows a sectional view of the dispensing device of FIG. 10A taken along the plane B-B in FIG. 10B.

FIG. 10C shows a second sectional view along the plane B-B in FIG. 10B. This figure shows that the push button 15 is, when the cap 24 is closed, actuated to the second orientation and a strip 17 is partially exposed, when the cap 24 is opened the next time.

According to the above described embodiment, it is possible to dispense a test strip 17 for analyzing a sample of bodily fluid from a dispensing device 10 in an easy and comfortable way without the risk of deformation of the test strip 17 and without unsatisfying tolerances. Thereby, the object of the invention is solved by this preferred embodiment.

Figure 11A:
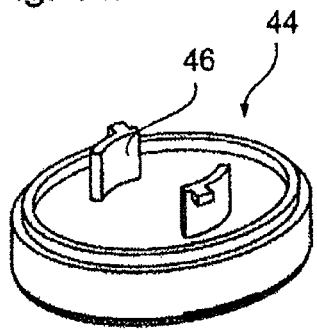
FIGS. 11A to 11E show a preferred embodiment of a double bottom of the dispensing device.
Figure 11B:
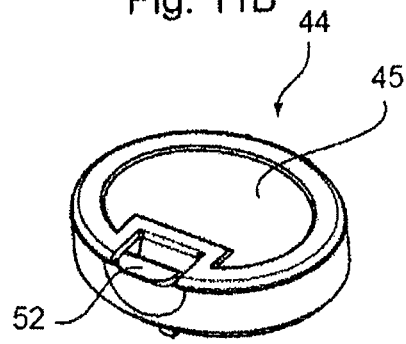

FIGS. 11A to 11E show a preferred embodiment of the bottom 44 of the dispensing device 10. In this preferred embodiment, the bottom 44 is provided as a double bottom and is configured to store used strips, a blood lancet or the like. The bottom 44 is shown in FIG. 11A in top view and the bayonet system 46 is seen. FIG. 11B shows the same bottom 44 in bottom view, i.e. from below. A tab 52 is illustrated by which the double bottom 45 can be opened. Similar mechanisms are possible for allowing the double bottom 45 to be opened.

Figure 11C:
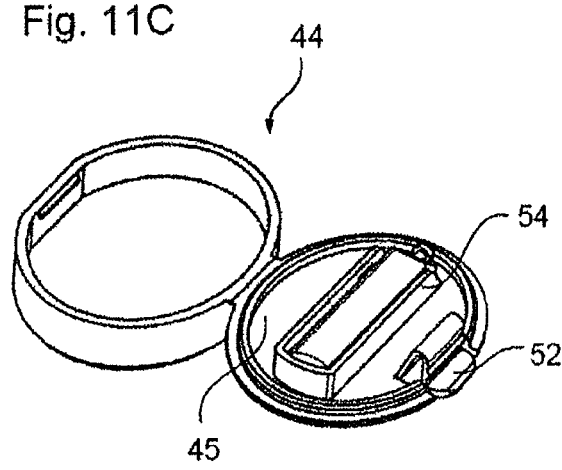
Figure 11D:
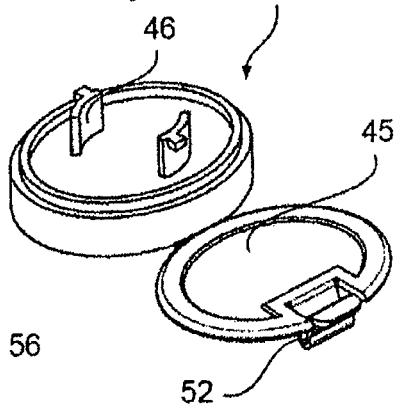

FIG. 11C illustrates the opened bottom 44 in a bottom view and a securing means 54 is illustrated which is configured to secure used test strips, a lancet or any other suitably sized element in a space inside of the bottom 44. FIG. 11D illustrates the opened state of the bottom 44 in a top view.

Figure 11E:
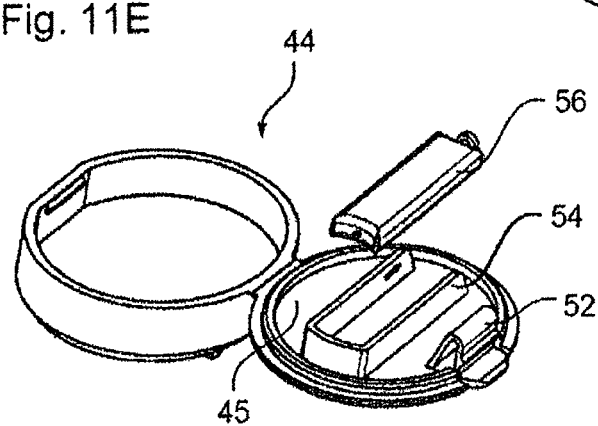

FIG. 11E shows basically the same view as FIG. 11C but with a blood lancet 56 which is suitably sized for it to be placed in and secured by the securing means 54. When closing the bottom 44, the blood lancet 56, or whatever is enclosed inside of the bottom 44, can be securely stowed while being easily accessible, if required.

The invention claimed is:

1. A dispensing device for holding and dispensing strip-like objects, like test strips for analyzing a sample of bodily fluid, wherein the dispensing device is configured to hold a stack of strips and comprises
   a container portion for holding the stack of strips; and
   a dispenser portion for dispensing strips from the dispensing device, one at a time;
   wherein the dispenser portion comprises a movable element for applying a rotational motion to the strip to be dispensed from a first orientation, in which the strip is enclosed in the dispensing device, to a second orientation, in which the strip is at least partially exposed,
   wherein the dispenser portion further comprises a clear space configured for containing a portion of the strip to be dispensed in its second orientation and allowing the strip to rotate into the second orientation,
   wherein the dispenser portion further comprises a fulcrum for the rotational motion of the strip, wherein the rotational motion of the strip is the result of two forces applied to the strip, namely a first force of the movable element on the strip pushing the strip using a longitudinal side of the strip, and
   a second force of the fulcrum defined in the dispenser portion on an opposed longitudinal side of the strip, and
   wherein the container portion is of a cylindrical shape and wherein the dispenser portion is situated at one of two axial ends of the container portion.

2. The dispensing device according to claim 1, wherein the rotational motion applied by the dispenser portion to the strip is parallel to a plane of the strip, wherein the rotational motion of the strip is about an axis of rotation that is perpendicular to the plane of the strip and is situated on a longitudinal side of the strip.

3. The dispensing device according to claim 1, wherein the dispenser portion is configured for exposing only a part of the strip.

4. The dispensing device according to claim 1, wherein the dispenser portion further comprises a recess for facilitating grabbing of the strip in the second orientation.

5. The dispensing device according to claim 1, wherein the container portion further comprises a spring for applying a spring force to the stack of strips in a spring force direction toward the dispenser portion.

6. The dispensing device according to claim 5, wherein the dispenser portion is configured for applying a rotational motion to the strip about an axis of rotation which is oriented in parallel to the spring force direction.

7. The dispensing device according to claim 5, wherein the container portion further comprises a piston pressing against the spring toward the stack of strips.

8. The dispensing device according to claim 7, wherein the piston further comprises a desiccant material.

9. The dispensing device according to claim 1, wherein the container portion further comprises a stack of 25 to 50 strips.

10. The dispensing device according to claim 1 further comprising a spare cartridge containing a stack of strips.

11. A cartridge containing the stack of strips configured for the dispensing device according to claim 10, comprising a clear space containing a portion of the strip and allowing the strip to rotate into the second orientation.

12. The cartridge according to claim 11, further comprising a window configured to allow passing of a portion of the movable element for rotating the strip contained in the cartridge.

13. The dispensing device according to claim 7, wherein the piston contains a desiccant material.

* * * * *